(12) United States Patent
Pardue et al.

(10) Patent No.: US 6,767,332 B1
(45) Date of Patent: Jul. 27, 2004

(54) ACTIVE ANKLE SUPPORT

(75) Inventors: Chris C. Pardue, 6203 Belle Aire Dr., Brentwood, TN (US) 37027; James A. Davidson, Germantown, TN (US)

(73) Assignee: Chris C. Pardue, Brentwood, TN (US)

( * ) Notice: Subject to any disclaimer, the term of this patent is extended or adjusted under 35 U.S.C. 154(b) by 0 days.

(21) Appl. No.: 09/583,476

(22) Filed: May 31, 2000

(51) Int. Cl.[7] .................. A61F 5/00; A61F 5/37
(52) U.S. Cl. .................. 602/27; 602/23; 128/882
(58) Field of Search .................. 602/5–8, 23, 27, 602/62, 65; 128/882

(56) References Cited

U.S. PATENT DOCUMENTS

| | | | |
|---|---|---|---|
| 2,994,322 A | * 8/1961 | Cullen et al. .................. 128/80 |
| 3,805,773 A | 4/1974 | Sichau .................. 128/80 |
| 3,970,083 A | 7/1976 | Carrigan .................. 128/166 |
| 4,187,844 A | 2/1980 | Caprio, Jr. .................. 128/166 |
| 4,280,488 A | 7/1981 | Polsky et al. .................. 128/80 H |
| 4,280,489 A | 7/1981 | Johnson, Jr. .................. 128/80 H |
| 4,289,122 A | 9/1981 | Mason et al. .................. 128/82 E |
| 4,299,211 A | * 11/1981 | Doynow .................. 128/869 |
| 4,323,058 A | 4/1982 | Detty .................. 128/80 H |
| 4,378,793 A | 4/1983 | Mauldin et al. .................. 128/80 H |
| 4,414,965 A | 11/1983 | Mauldin et al. .................. 128/87 R |
| 4,572,167 A | * 2/1986 | Brunswick .................. 602/5 |
| 4,665,904 A | * 5/1987 | Lerman .................. 602/27 XZ |
| 4,716,892 A | * 1/1988 | Brunswick .................. 602/64 |
| 4,771,768 A | * 9/1988 | Crispin .................. 128/88 |
| 4,934,355 A | * 6/1990 | Porcelli .................. 128/80 H |
| 4,974,583 A | 12/1990 | Freitas .................. 128/80 R |
| 4,977,891 A | 12/1990 | Grim .................. 128/80 H |
| 5,031,607 A | 7/1991 | Peters .................. 128/80 H |
| 5,078,128 A | 1/1992 | Grim et al. .................. 128/83.5 |
| 5,242,379 A | 9/1993 | Harris et al. .................. 602/27 |
| 5,250,021 A | 10/1993 | Chang .................. 602/27 |
| 5,366,439 A | * 11/1994 | Peters .................. 602/27 |
| 5,368,551 A | 11/1994 | Zuckerman .................. 602/23 |
| 5,496,263 A | * 3/1996 | Fuller, II et al. .................. 602/27 |
| 5,501,659 A | 3/1996 | Morris et al. .................. 602/27 |
| 5,536,544 A | * 7/1996 | Liegeois .................. 428/36.1 |
| 5,549,678 A | * 8/1996 | Prostkoff .................. 623/16 |
| 5,584,799 A | * 12/1996 | Gray .................. 602/5 |
| 5,611,773 A | * 3/1997 | Nash et al. .................. 602/16 |
| 5,620,411 A | 4/1997 | Schumann et al. .................. 602/23 |
| 5,672,150 A | * 9/1997 | Cox .................. 602/21 |
| 5,676,642 A | 10/1997 | Peters .................. 602/27 |
| 5,681,269 A | * 10/1997 | Basaj .................. 602/22 |
| 5,759,168 A | * 6/1998 | Bussell et al. .................. 602/27 |
| 5,797,865 A | 8/1998 | McDavid, III .................. 602/27 |
| 5,810,754 A | 9/1998 | Kenosh .................. 602/27 |
| 5,833,639 A | * 11/1998 | Nunes et al. .................. 602/23 |
| 5,868,693 A | 2/1999 | Duback et al. .................. 602/27 |
| 5,899,872 A | 5/1999 | Gilmour .................. 602/65 |
| 5,908,398 A | 6/1999 | DeToro .................. 602/16 |
| 5,944,678 A | 8/1999 | Hubbard .................. 602/27 |
| 5,951,504 A | 9/1999 | Iglesias et al. .................. 602/27 |
| 5,957,871 A | 9/1999 | Darcey .................. 602/12 |
| 5,980,474 A | 11/1999 | Darcey .................. 602/5 |
| 6,022,331 A | 2/2000 | Darcey .................. 602/12 |

* cited by examiner

Primary Examiner—Nicholas D. Lucchesi
Assistant Examiner—Fenn C Mathew
(74) Attorney, Agent, or Firm—Fulbright & Jaworski L.L.P.

(57) ABSTRACT

An ankle support for protecting an injured or uninjured ankle which includes lateral support members having a flexion region operable to limit plantar and dorsal flexion to 40 degrees. Lateral support members are connected with lower-leg supports which together act to limit rotation to 15 degrees and medial and lateral bending to 10 degrees. Ankle support is preferably contoured with a low component-profile such that ankle support can be worn within a shoe to provide user with support and stabilization during rigorous activity. Adjustable straps are utilized to firmly engage ankle support with user's lower leg which operably reduces or minimizes load to the foot. Ankle support component parts are preferably formed from a low melting temperature thermo-forming polymer, polymer alloy, or composite material which provides the user with an advantageous ankle support and method for maintaining ankle supports fit to the lower leg.

17 Claims, 2 Drawing Sheets

ACTIVE ANKLE SUPPORT

FIELD OF THE INVENTION

The present invention relates to an ankle support to either reduce the tendency for ankle injury or to reduce further injury to an injured ankle during physical activity in which the ankle maybe subjected to potentially injurious loads and displacements. The ankle support is designed to be form fitting to the portion of the leg above the ankle to reduce or eliminate loading to the foot. The ankle support includes a platform (heel stirrup) to align the foot and is adapted to be inserted into a shoe. Adjustable straps or other suitable attachment assemblies are used to secure the support device to the user.

BACKGROUND OF THE INVENTION

Today, an increasing number of individuals are engaging in more active life styles. Such an increase is leading to a proliferation of active involvement in sporting activities, such as basketball, football, baseball, tennis, soccer, skiing, jogging, and the like. Participating in both recreational and professional sports and other healthier activities, including "weekend athletes", may aggravate an existing ankle injury, or may injure a previously healthy ankle. There is therefore a substantial need for an active ankle support to reduce and minimize the potential for initial or further ankle injury. Additionally, it is useful to have such a device adapted to be fitted by the user, and which can fit within the shoe for active wear.

A common injury to the ankle is ligament damage. This injury is quite painful and may require months to heal. The increased incidence of such injuries, and the desire of the injured individual to continue with a healthy, active level of sports and exercise, requires an ankle support which can reduce or eliminate loading on the foot, and thus the injured ligaments. To be used during active participation in physical activity, however, it must be able to be worn with the type of shoe required for that particular activity. Individuals as well can use the same support to reduce the likelihood of incurring an ankle injury.

In the past, athletes often relied on taping or wrapping an ankle to provide support. Such support, however, creates a limited amount of mobility, and may even hinder the effectiveness of a particular activity. It also requires special training and know how to properly wrap the ankle to reduce injury. As such, the "weekend athlete" is often unable to properly apply taping, wrapping, or other support device on his or her own.

There are numerous varieties of ankle braces available covering a wide spectrum of stabilization and design characteristics. Some are custom fit, some allow unrestricted or excessively restricted motion, some require excessive strapping, and even others require specific control of the talus and other anklebones. None of the current devices, however, allows for a combination of the following: a) a restrictive support formed from flexible polymer support material operable to engage and allow an additional amount of flexion, rotation, or extension during more severe loading events; b) a support capable of reducing or eliminating load to the foot; c) conformable and easy to use polymer supports and flexible straps for firmly securing the support to the ankle and lower leg of the user; and, d) ability to place a shoe over the support so as to allow continued participation in a sporting activity. These features along with padding or cushioning are the basis of the ankle support of the present invention. The need for an ankle support with these functional characteristics, as well as one which is easy to use, inexpensive, off-the-shelf and actively functional, is readily apparent.

Though numerous ankle supports have been previously described, none describe the use of a conformal, reshapeable, controlled range of motion (ROM) ankle support which reduces loading on a foot and can be worn in a shoe. For example, U.S. Pat. No. 5,676,642 by R. Peters describes an active ankle device that is modular, has uncontrolled ROM, and does not reduce loading to the foot. Further, it is not designed to be worn within a shoe. U.S. Pat No. 5,368,551 by R. Zuckerman, U.S. Pat. No. 5,250,021 by S. Chang, U.S. Pat. No. 5,078,128 by T. Grim and T. Kasper, U.S. Pat. No. 4,414,965 by D. Mancdin and R. Jones, U.S. Pat. No. 5,031,607 by R. Peters, and U.S. Pat. No. 4,974,583 by M. Freitas each describe ankle support devices. These supports, however, are modular, complicated, cumbersome, and do not specify specific ROM. Furthermore, they cannot fit within a shoe, and do not reduce load to the foot.

U.S. Pat No. 5,242,379 by Harris et al. describes an ankle brace having a floating pivot hinge. The ankle support of the present invention does not in corporate such a hinge. Further, the present invention reduces load to the foot and can fit within a shoe, unlike the '379 Patent. In U.S. Pat No. 5,797,865 by R. Finley, a light-weight plastic ankle restraint is described to limit movement of an injured ankle. However, it does not reduce load to the foot and is not capable of being inserted into a shoe during active wear as is the present invention. U.S. Pat. No. 5,496,263 by N. Fuller et al. describes an ankle brace having at least one single taloric control device. Importantly, the '263 Patent does not restrict loading to the foot and is not designed to be inserted into a shoe.

U.S. Pat. No. 4,977,891 by T. Grim describes an ankle support with inflatable bladders attached to rigid side supports. It does not allow for reduced loading to the foot nor can it be inserted into a shoe as with the present invention. U.S. Pat. No. 5,951,504 by J. Iglesias et al. describes an ankle brace having an adjustable heel strap together with rigid side supports, and made of a flexible resilient material. Although the present invention takes advantage of flexible, resilient materials, the '504 Patent does not reduce loading to the foot and is not designed to be worn within a shoe. Furthermore, the allowable ROM is not defined as for the present invention.

U.S. Pat. No. 5,944,078 by C. Hubbard describes a support which allows loading on the foot and full ROM of the ankle in contrast to the present invention. U.S. Pat. No. 5,908,398 by Harris restricts ankle motion, but again, does not restrict loading on the foot nor allows for a shoe to be worn over the device. U.S. Pat. No. 5,368,551 by R. Zuckerman describes another leg and foot support device with lateral support struts, adapted to snap into the footplate. The footplate is curved to allow a rolling motion against the foot, but does not restrict load to the foot as in the present invention. The '551 Patent further states that current ankle support designs are weak and can break at the junction between the struts and foot boot, and that cracking in this region may exacerbate ankle injury. The present invention is specially designed to be disposable so as to avoid or reduce this additional aspect of ankle support design and performance.

U.S. Pat. No. 5,620,411 by G. Schumann describes an ankle brace that allows the inherent elastic properties of the device material to provide an unspecified amount of ROM.

However, there is no description of restricting load to the foot or allowance for the device to be inserted into a shoe. U.S. Pat. No. 5,501,659 by J. Morris and J. Stetman describes a brace to inhibit inversion and aversion of the ankle while also accommodating plantar and dorsal flexion. The present invention restricts the latter flexion motion and also reduces load transferred to the foot, unlike the '639 Patent. U.S. Pat. No. 5,899,872 by R. Gilmour describes a foot and ankle support having a boot element and shaped components for the lower leg. The Gilmour support may also include a complete shell. Unlike the present invention, ROM restrictions are not defined, nor does the '872 ankle support restrict loading to the foot.

There are also several Patents from between 1974 and 1983 that describe ankle supports having non-specified restrictions ROM, foot and lower-leg attachment straps to secure the support in place, and the use of elastic materials and lateral supports. These include U.S. Pat. Nos. 3,805,773 (4/74), 3,970,083 (7/76), 4,187,844 (2/80), 4,280,488 (7/81), 4,280,489 (7/81), 4,289,122 (9/81), 4,323,058 (4/82) and 4,378,793 (4/83). As with the case of the more recent Patents previously discussed, these Patents do not describe reduced loading to the foot, specific ROM restrictions, reshaping, or the ability of a shoe to be worn over the ankle support.

It is accordingly an object of the present invention to provide an ankle support which reduces and minimizes the potential for initial or further ankle injury during sporting or other physical activities by limiting an ankles range of motion to 40 degrees plantar and dorsal flexion, 15 degrees rotation, and 10 degrees medial or lateral angulation.

Another object of the present invention is to provide an ankle support having component parts formed from a thermo-forming material that allows a user to readily contour the ankle support to the user's particular body shape by simply heating support, reshaping support, and allowing it to return to its natural state upon cooling.

Another object of the present invention is to provide a conformable ankle support manufactured as one basic design so as to reduce the need for the more expensive production of left and right ankle supports.

Another object of the present invention is to reduce loading of ground forces to a user's foot by transferring the load from a load bearing foot member to the user's lower-leg.

Another object of the present invention is to provide lateral support members operable to undergo plantar flexion and dorsal flexion motion during physical activity.

A further object of the present invention is to provide an ankle support adapted to be inserted into a shoe.

A still further object of the present invention is to provide an ankle support characterized by low-cost molding and manufacturing.

Other objects and advantages of the present invention will become apparent from a reading of the detailed description of the invention in connection with the accompanying drawing.

SUMMARY OF THE INVENTION

The present invention relates to an ankle support specially adapted to allow plantar and flexion motion while reducing loading forces normally absorbed by the foot during activity. Specifically, the ankle support of the present invention includes four distinct component parts: a foot member, a pair of lateral support members, one or more lower-leg support members, and flexible straps to secure the ankle support to the user's lower-leg, ankle and foot. More particularly, the presently disclosed ankle support provides a load bearing foot support adapted to receive a foot, and transfer ground loading forces away from the foot through a pair of connected lateral side support members configured in load transferring communication with one or more lower-leg support members. The lower-leg support members are preferably configured to encompass and provide firm supporting engagement to the lower-leg. In this way, ground forces are operably transferred from the foot support to the lower-leg support member and to the lower-leg such that loading to a foot is reduced or minimized. To facilitate plantar flexion and dorsal flexion of the user's foot and ankle, the pair of lateral supports are formed from a polymer material, and include a flexion region defining a reduced lateral cross-sectional area within an intermediate portion of each lateral support.

BRIEF DESCRIPTION OF THE INVENTION

DETAILED DESCRIPTION OF THE PREFERRED EMBODIMENT

Figure 1:
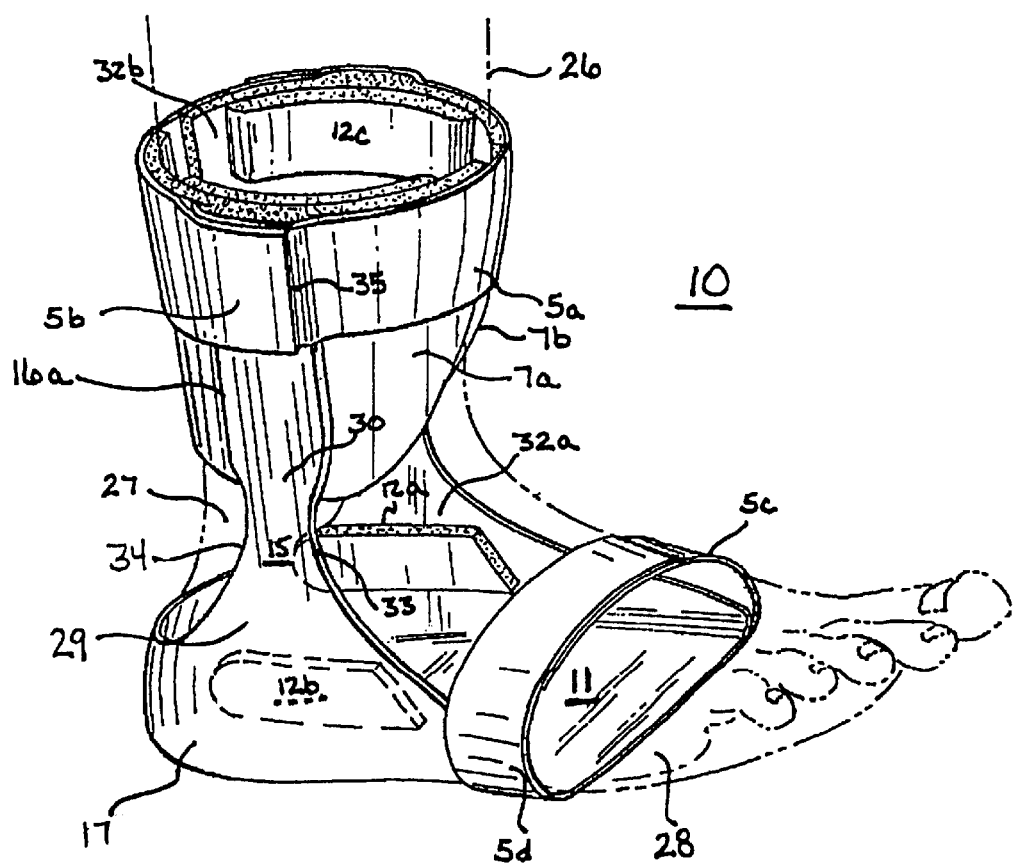
FIG. 1 is a perspective view of the ankle support of the present invention fitted and properly secured to the right foot of a user.
Figure 2:
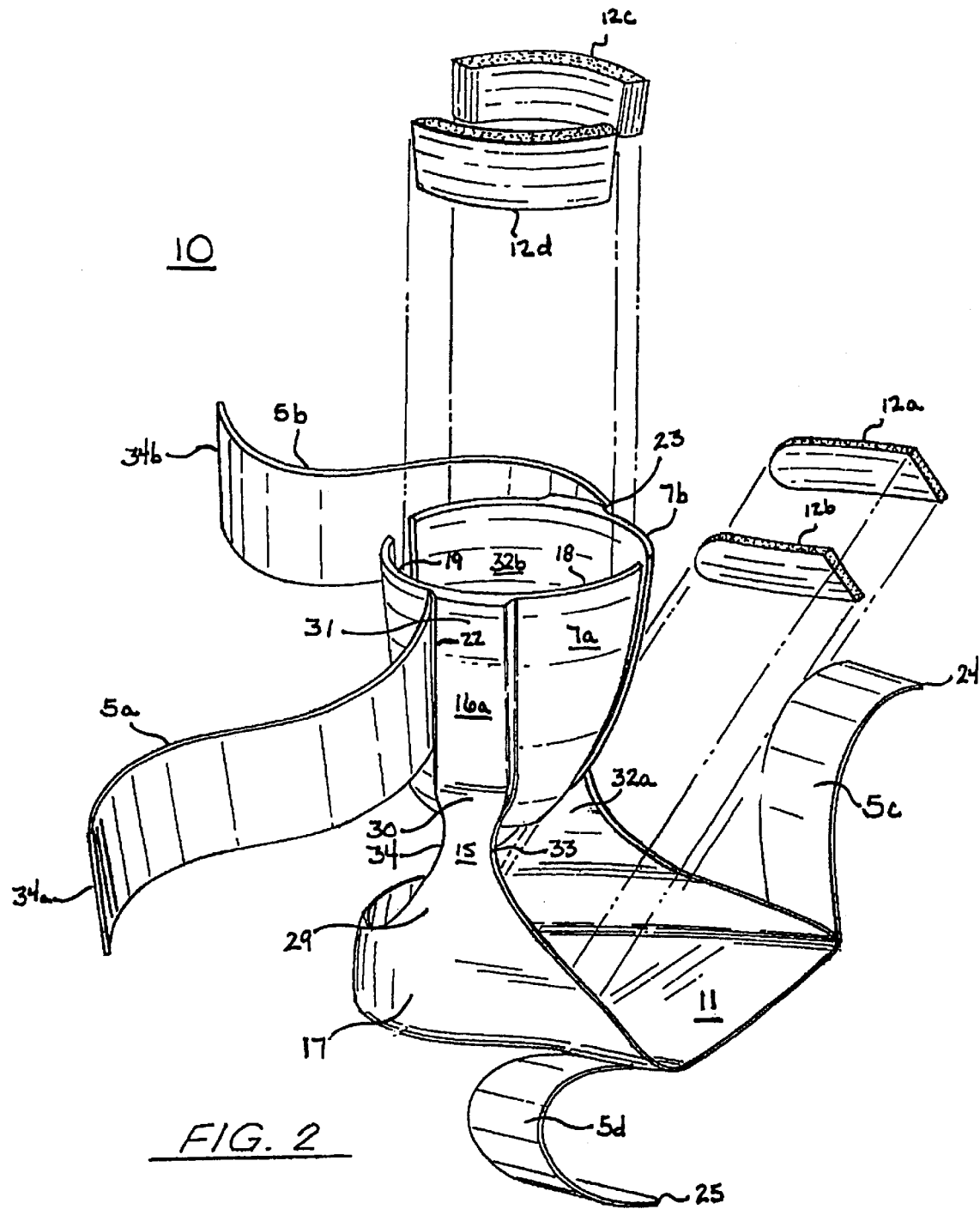
FIG. 2 is a partially exploded perspective view of the ankle support of the present invention.

A preferred ankle support (10) of the present invention is illustrated in FIGS. 1 and 2. As shown, an ankle support (10) of the present invention comprises a heel stirrup or load bearing foot support (11) connected to a pair of lateral support members (16a–b). A pair of lower leg support members (7a–b) for encompassing and firmly holding the lower leg (26) are connected to an upper portion (31) of lateral support members (16a–b). To maintain the ankle support (10) in a fixed position about user's lower leg (26) and ankle (27), flexible attachment straps (5a–d) are provided. Together, lateral support members (16a–b) and lower-leg support members (7a–b) operably limit rotation, plantar flexion and dorsal flexion, and medial and lateral angulation of the ankle (27) and foot (28).

In a preferred embodiment, foot support (11) is adapted to hold and align foot (28) thereby properly positioning each lateral support (16a–b) and each lower-leg support (7a–b) about the ankle (27) and lower-leg (26). Foot support (11) is preferably configured to be worn within a shoe, thus allowing use of the ankle support (10) during physical activity. To permit the foot support (11) to be worn within a shoe, foot support (11) is designed to be highly conformal and fit substantially adjacent to a user's foot. It is therefore preferred that foot support (11) have a low profile without any unnecessary protrusions on support's (11) outer surface. As illustrated in FIGS. 1 and 2, foot support (11) is integrally connected to each lateral support member (16a–b) without using connectors that could prohibit proper insertion of foot support (11) into a shoe.

Foot support (11) is preferably formed from a polymer or polymeric composite material. As discussed below, the polymer material is preferably a thermo-forming polymer. In this way, an ankle support (10) user can moldably shape and fit the foot support (11) to the individual contours of his or her lower leg, anfle and foot (28). Such self-fitting provides the user with a readily available method for continuously maintaining a desired contour and fit for the foot support (11). In this manner, an individual user can customize the foot support (11), and thereby obtain a fit that is more beneficial to a particular use, physical activity or injury.

As illustrated in FIG. 1, each lateral support member (16a–b) comprises a lower portion (29) integrally connected with the rear heel portion (17) of foot support (11). Each lateral support member (16a–b) is therefore disposed adjacent to opposite sides of a user's leg. A preferred ankle support (10) comprising foot support (11), lateral support members (16a–b) and lower-leg support members (7a–b) is manufactured as a unitary body using injection molding techniques well known in the art. Such construction provides for an ankle support (10) having a smooth, low profile; especially at the transition points between the respective support members. Alternatively, lower-leg support members (7a–b) can be attached to lateral supports (16a–b), and lateral supports (16a–b) to the foot support (11) using heat molding techniques generally known in the art. It should be understood, however, that any combination of injection molding and heat molding techniques can be used without to deviating from the scope of the present invention.

As further illustrated, each lateral support member (16a–b) includes an intermediate portion (30) extending upwards along the inner and outer sides of the ankle (27), and an upper portion (31) terminating at a position adjacent to the lower leg (26). Each lateral support member (16a–b) can be contoured to fit firmly about the sides of the ankle (27), thereby substantially limiting medial and lateral angulations of the ankle. In one embodiment, lateral supports (16a–b) can be provided with recessed inner surfaces (not shown) contoured to provide firm supporting engagement with the medial and lateral surfaces of a user's ankle (27). Preferably, and as further described below, each lateral support member (16a–b) is provided with a generally flat moldable inner surface (32) for allowing the user to customize the supports (10) fit to his or her ankle (27). Specifically, each lateral support (16a–b) is conformed to the particular contours of the user's medial and lateral ankle surfaces by heating the lateral support (16a–b) to a pliable condition and molding them to fit firmly against the user's ankle (27) and lower leg region.

Referring to FIGS. 1 & 2, lateral support members (16a–b) are provided as a continuous support member defining a notched flexion region (15) that allows limited dorsal or plantar flexion motion. As shown, the preferred flexion region (15) is defined by each lateral support member (16a–b) having a reduced lateral cross-sectional area substantially within the intermediate portion (30) of the respective lateral support member (16a–b). It is to be understood that substantially within the intermediate portion preferably includes that portion of the lateral support member (16a–b) adjacent to the user's ankle (27). The flexion region (15) is formed in each lateral support member (16a–b) as a pair of recessed curved or concave surfaces located on opposing front (33) and back (34) vertical surfaces of each lateral support member (16a–b). Alternatively, the front (33) and back (34) vertical surfaces can define recessed surfaces of alternative form or shape. For example, a flexion region (15) could be defined by a triangulated recessed surface, or a recessed surface having a multifaceted surface (not shown). Additionally, the front surface (33) of the flexion region (15) can define a greater or lesser recess relative to the back surface (34) of the flexion region (15), or visa versa. In this manner, a flexion region (15) can have variable degrees of dorsal and plantar flexion motion. More particularly, a surface (33 or 34) having a greater recess or more reduce lateral cross-sectional area relative to the opposing surface can undergo greater bending in response to flexion motion forces.

In use, the flexion region (15) undergoes limited dorsal or plantar flexion motion in response to dorsal flexion and plantar flexion forces. For example, when the user of ankle support (10) subjects the flexion region (15) to plantar flexion (forward flexing), the upper and lower portions of each lateral support member (16a–b) remain in a generally fixed position. The flexion region (15), however, engages and provides limited flexing or bending of the ankle (27). Thus, the user's ankle (27) is not maintained in a rigid conformation, but is provided with a limited range of plantar and dorsal flexing motion such that the user can continue to participate in physical activity.

It should be understood that the particular degree of dorsal or plantar flexion motion allowed by the flexion region (15) is dependent upon the cross-sectional area of the flexion region (15), and the elastic modulus value of the particular polymer used to construct the flexion region (15). Specifically, less flexing is allowed with a thicker flexion region (15), and more flexing with a thinner flexion region (15). It is therefore to be understood that the relative flexibility or rigidity of the flexion region, and as such, the range of dorsal or plantar flexion motion can be adjusted to achieve varying degrees of motion by modifying the material modulus and the cross-sectional area of the flexion region (15).

Though each lateral support member (16a–b) includes a preferred flexion region (15), the ankle support (10) can also included a hinge at the transition between a lateral support (16) and the foot support (10) (not shown). Alternatively, lateral supports (16a–b) may incorporate a hinge at a position above the foot support (not shown). To ensure that the support (10) can be used with a shoe, the hinge is preferably constructed flush with the outer surface of the support (10).

As illustrated in FIG. 2, lateral support members (16a–b) are integrally coupled with lower leg support members (7a–b) that wrap around and securely engage the lower leg (26). Each lower leg support member (7a–b) has an arcuate shaped front (18) and back (19) surface extending away from and perpendicular to each lateral support member (16a–b) for encasing the lower leg (26). Once the lower leg (26) is firmly supported by lower leg supports (7a–b), the supports (7a–b) together with lateral supports (16a–b) operably limit the ankles range of motion. In a preferred embodiment, supports (7a–b and 16a–b) are constructed from an elastic polymer material having a thickness sufficient to limit rotation to 15 degrees and medial or lateral angulations to 10 degrees.

Support members (7a–b and 16a–b) are designed to provide a close, contoured fit about the lower leg (26) and ankle (27). Providing a firm fit increases stability to the lower leg (26), and operably reduces load to the foot (28). More specifically, foot support (11) is adapted to transfer ground loading forces through each connected lateral support (16a–b) and onto each lower-leg support (7a–b). Each lower leg support (7a–b) is adapted to firmly hold and support the lower leg (26), and thus, is in force communication with the lower leg. As ground forces are received by the foot support (11), the forces are transferred through each lateral support (16a–b) and to each lower leg support (7a–b). The ground forces are then transferred onto the conformal, firmly held lower leg (27), which prevents initial or further injury to ankle (27).

As shown in FIG. 2, it is preferable to utilize two separate lower leg supports (7a–b) to encase the user's lower leg (26). More particularly, constructing ankle support (10) with separate lower leg supports (7a–b) provides front (20) and back (21) vertical spaces that allow the lower leg supports (7a–b) to be moved apart from each other so as to more easily receive a wide range of foot, ankle and lower-leg sizes.

As illustrated in FIGS. 1 and 2, ankle support (10) comprises one or more flexible straps (5a–d) configured to securely fasten the ankle support (10) to the user, thereby providing firm support about the foot, ankle and lower-leg. In a preferred embodiment, two flexible straps (5a–b) are provided to secure the lateral (16a–b) and lower leg supports (7a–b) about the user's ankle (27) and lower leg (26). As illustrated, a first strap (5a) is attached to the back upper vertical surface (22) of lateral support (16a), and a second strap (5b) is attached to the front upper vertical surface (23) of the opposite lateral support (16b). The free ends (34a–b) of each strap (5a–b, respectively) include an adhesive surface, such as VELCRO®, adapted to releasably mate with a matching adhesive surface located on the outer surface (35) of the opposing strap (5a–b). Specifically, each strap end (34a–b) is provided with hook adhesive material, .and the outer surface (35) of the opposing strap (5a–b) includes a loop adhesive material adapted to releasably connect with the hook adhesive material. In use, the user positions the ankle support (10) about his or her foot, ankle and lower leg and wraps the first strap (5a) across the front of the lower leg and secures free end (34a) to the adhesive surface located on outer surface (35) of opposing strap (5b). The second strap (5b) is then extended across the back of the lower leg and secured to adhesive surface (not shown) on the outer surface (35) of the first strap (5a). With this strap arrangement, the user is able to tightly draw the lateral (16a–b) and lower leg supports (7a–b) about the lower leg so as to firmly engage and properly support the ankle and lower leg. It should be understood that varying configurations of straps for securing the ankle support (10) to a foot, ankle and lower leg can be utilized without deviating from the scope of the present invention. Such other means can include straps that utilize buckle or snap connectors.

As further illustrated in FIGS. 1 and 2, a pair of flexible straps (5c–d) are provided to firmly engage the user's foot (28). As shown in FIG. 2, one strap (5c) is connected to one side of foot support (11), and the other strap (5d) is connected to the opposing side of foot support (11). Alternatively, straps (5c–d) compromise a single strap that is attached to the bottom surface of support (11), and includes two free ends which attach above the foot (28). Strap (5c) includes a free end (24) with hook material and the opposing strap (5d) has a free end (25) with loop material adapted to releasably attach to the hook material. In use, straps (5c–d) are pulled firmly across the upper surface of the foot (28) and the free ends are releasably attached to hold foot support (11) in proper alignment with the foot (28).

Pads or cushions (12a–d) are optionally provided to further reduce load to the foot and prevent the development of rubbing sores or blisters due to resulting frictional forces between the skin surface and the inner surface (32) of the ankle support (10). As shown in FIG. 1, pads (12a–d) are preferably positioned along the inner surface (32a–b) of the foot support (11), and lower leg supports (7a–b), respectively. Another advantage of using pads (12a–d) is their capability to distribute and transfer load away from the foot (28) and lower leg (26). Pads (12) can be permanently or releasably attached; however, as shown in FIG. 2, it is preferable to provide pads as a releasable and adjustable component so the user can position the pads (12) as desired. Additionally, removable pads (12) allow a user to remove them as they may become worn and ineffective. Pads (12) can also be provided as adjustable inflatable air bladders, thereby allowing the user to alter the degree of support and stabilization to the lower leg as may be required to accommodate more rigorous physical activity or serious injury.

It is preferred that one or more component parts of the ankle support (10) be made from a polymer, a polymeric material, a fiber reinforced polymer composite material, a low modulus metal, or any combination thereof. The component material is preferably tough and moderately rigid having an elastic modules between about 0.5 and 4.0 msi. In addition, the present invention is preferably formed of a polymer or polymeric composite material having thermo-forming properties that allow the component parts to be formed using commonly known heat-shrinking methods of manufacture commonly known in the art. More particularly, lateral supports (16a–b) and lower-leg supports (7a–b) are preferably made from a moldable low-temperature or heat-shrinking thermoplastic elastomer having an elastic modulus between about 0.5 to 4 msi. If a metal is incorporated to reinforce the polymer or polymer alloy, it is preferable that the utilized metal be characterized by a modulus value of between about 4 to 15 msi.

In another preferred embodiment, an ankle support (10) is made from a thermo-polymer that can be re-adjusted by simply dipping the support in a hot liquid (e.g. water) until the support becomes pliable, reshaping the support, and allowing the re-contoured support regions to return to a natural, rigid state at ambient temperatures. This method of adjusting the present invention provides the user with a substantial advantage in that the user can conform the ankle support (10) to his or her own particular body contours. In this way, the user can adjust the shape of the ankle support to accommodate decreased swelling in the ankle or lower-leg regions, or refitting as may be needed for an alternative activity. Preferably, the component parts, including lateral supports (16a–b), lower leg supports (7a–b), and foot support (11) are formed from a thermo-polymer, or thermo-polymer alloy capable of being molded and shaped at temperatures between about 50° and 100° C. Thermo-polymers suitable for use with the present invention include polycaprolactone, transpolyisoprene, system butadiene-styrene acrylic-based resin polymers, including ethylene, acrylic ester and ethylene methyl acrylate thermoplastics and their various copolymers, epoxy modified polyolefins and the like. It should be understood, however, that numerous other thermoplastic elastomers are available for use in the present invention without deviating from the scope of the present invention. It should be further understood that the polymers and polymer alloys can be compounded with to produce component parts of differing flexibility, rigidity and strength. Such fillers can include, but are not limited to, silica and/or silicate-based mineral fillers, iron oxides, titanium oxides and magnesium compounds.

In an advantageous use of the present invention, the user is provided with an thermo-forming ankle support (10) which can be readily and easily fitted to the user's foot (28) and lower leg (26), as well as re-contoured or reshaped as may be needed. Specifically, the user can conveniently shape the ankle support (10) to fit a particular lower leg shape by simply placing at least a portion of it into a liquid having a temperature at least above the melting temperature of the thermo-forming polymer used to make the component parts of ankle support (10). For example, thermo-polymer ethylene-acrylic ester has a melting temperature of about 60° C., and as such, an ankle support (10) of the present invention formed of this polymer can be reshaped by placing it into hot water at a temperature above 60° C. Once the polymer is pliable, the user can place the ankle support about the lower leg and reshape it to the lower leg by hand. After the ankle support is fitted to the user, the support will maintain that shape at ambient temperatures. Thus, the user can adjust the fit of the ankle support (10) as swelling or other injury related changes subside, and the ankle returns to its normal pre-injury shape. Depending on the filler and nature of the ethylene-acrylic ester composition, the melting temperature may be adjusted to a range of between about 60–70° C.

One skilled in the art will readily appreciate that the invention is well adapted to carry out the objects and obtain the ends and advantages mentioned as well as those inherent therein. One skilled in the art will also readily appreciate that the elements described herein but not shown are all considered to be known to one skilled in the art of packaging machines. Active ankle support of the present invention described herein are presently representative of the preferred embodiments, are exemplary and are not intended as limitations on the scope of the invention. Changes therein and other uses will occur to those skilled in the art which are encompassed within the spirit of the invention and are defined by the scope of the claims.

What is claimed is:

1. An ankle support comprising:
   a foot support member adapted to receive a foot;
   at least one lower-leg support member configured to encompass at least a portion of a lower-leg;
   a first lateral support member interconnecting one side of said foot member with said lower-leg support member;
   a second lateral support member interconnecting a second side of said foot member with said lower-leg support member;
   said first and second lateral support member having a continuous intermediate portion having a reduced lateral cross-sectional area so as to allow plantar flexion and dorsal flexion of each said lateral support member;
   wherein at least one of said first and second lateral support members, foot member, and lower-leg support member is formed from a thermo-forming polymer material, the thermo-forming polymer material shaped at a temperature in the range of about 50° to 100° C. wherein said thermo-forming polymer material has an elastic modulus of about 0.5 to 4.0 msi whereby said at least one support member can be heated and reshaped to conform to a user's ankle, foot or lower-leg.

2. An ankle support according to claim 1, wherein said thermo-forming polymer material is selected from the group consisting of polycaprolactone, transpolystyrene, butadiene-styrene, acrylic-based resin polymers, ethylene acrylic ester and its copolymer, ethylene methyl acrylate and its copolymer and epoxy modified polyolefins.

3. An ankle support of claim 1, wherein said continuous intermediate portion of said lateral support member having a reduced lateral cross-sectional area has a curved surface.

4. An ankle support of claim 1, wherein said continuous intermediate portion of said lateral support member having a reduced lateral cross-sectional area has a plurality of angled surfaces.

5. An ankle support of claim 1, further comprising one or more pads releaseably attached to as least a portion of an inner surface of said ankle support.

6. An ankle support of claim 1, further comprising one or more straps operable to securely fasten said ankle support in stable supporting engagement with the foot, ankle and lower-leg of a user.

7. An ankle support of claim 6, wherein said straps is at least one pair of straps, one of said pair of straps has a loop material and the other of said pair of straps has a hook material adapted to releasable connect with said loop material.

8. An ankle support of claim 6, wherein said straps includes at least one strap adapted to releasable connect with a surface of said ankle support, said strap has hook material and said surface of said ankle support has loop material adapted to releasable connect with said hook material.

9. An ankle support of claim 1, wherein said lower-leg support member is adapted to substantially encompass the lower-leg when positioned about the lower-leg.

10. An ankle support of claim 1, wherein said reduced lateral cross-sectional area of each said lateral support member is adapted to limit plantar flexion and dorsal flexion of each said lateral support member to about 40 degrees.

11. An ankle support comprising:
    a load bearing foot support adapted to receive a foot;
    a lower-leg support member configured to encompass at least a portion of a lower-leg;
    a continuous first lateral support member interconnecting one side of said load bearing foot support with said lower-leg support member;
    a continuous second lateral support member interconnecting a second side of said load bearing foot support with said lower-leg support member;
    wherein at least one of said lower-leg support member, foot member, and first and second lateral support members is formed from a thermo-forming polymer material, the thermo-forming polymer material shaped at a temperature in the range of about 50° to 100° C. wherein said thermo-forming polymer material has an elastic modulus of about 0.5 to 4.0 msi. whereby said at least one support member can be heated and reshaped in order to conform to a user's ankle, foot or lower-leg.

12. An ankle support of claim 11, further comprising an intermediate portion of each said continuous lateral support member having a reduced lateral cross-sectional area so as to allow plantar flexion and dorsal flexion of each said lateral support member.

13. An ankle support of claim 11, further comprising one or more straps operable to securely fasten said ankle support in stable supporting engagement with the foot, ankle and lower-leg of a user.

14. An ankle support of claim 11, further comprising one or more pads releasable attached to at least a portion of an inner surface of said ankle support.

15. An ankle support of claim 14, wherein at least one of said one or more pads is an inflatable air bladder.

16. An ankle support comprising:
    a foot support member adapted to receive a foot;
    at least one lower-leg support member configured to encompass at least a portion of a lower-leg;
    a first lateral support member interconnecting one side of said foot support with said lower-leg support member;
    a second lateral support member interconnecting a second side of said foot support with said lower-leg support member;
    at least one pad releaseably attached to at least a portion of an inner surface of said ankle support;
    at least one strap operable to securely fasten said ankle support in stable supporting engagement with the foot, ankle and lower-leg of a user;
    at least one of said lower leg support, foot support, and first and second lateral support members is formed from a thermo-forming polymer material, the thermo-forming polymer material shaped at a temperature in the range of about 50° to 100° C. wherein said thermoforming polymer material has an elastic modulus of about 0.5 to 4.0 msi. whereby said at least one support member can be heated and reshaped in order to conform to a user's ankle, foot or lower-leg; and, wherein each said lateral support member has a continuous intermediate portion having a reduced lateral cross-sectional area so as to allow plantar flexion and dorsal flexion of each said lateral support member.

17. An ankle support of claim 16, wherein said thermoforming polymer material is selected from the group consisting of polycaprolactone, transpolystyrene, butadiene-styrene, acrylic-based resin polymers, ethylene acrylic ester and its copolymer, ethylene methyl acrylate and its copolymer and epoxy modified polyolefins.

* * * * *